US008478401B2

(12) United States Patent
Freeman

(10) Patent No.: US 8,478,401 B2
(45) Date of Patent: Jul. 2, 2013

(54) SYNCHRONIZATION OF DEFIBRILLATION AND CHEST COMPRESSIONS

(75) Inventor: Gary A. Freeman, Newton Center, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 592 days.

(21) Appl. No.: 12/263,813

(22) Filed: Nov. 3, 2008

(65) Prior Publication Data

US 2009/0149903 A1 Jun. 11, 2009

Related U.S. Application Data

(60) Provisional application No. 61/001,347, filed on Nov. 1, 2007.

(51) Int. Cl.
*A61N 1/00* (2006.01)
(52) U.S. Cl.
USPC ......... 607/6; 607/4; 607/5; 607/119; 607/129
(58) Field of Classification Search
USPC ................ 607/4–6, 119, 129; 600/300, 513, 600/518
See application file for complete search history.

(56) References Cited

U.S. PATENT DOCUMENTS

| 4,198,963 | A | 4/1980 | Barkalow et al. |
| 5,626,618 | A | 5/1997 | Ward et al. |
| 5,957,856 | A | 9/1999 | Weil et al. |
| 6,112,117 | A | 8/2000 | KenKnight et al. |
| 6,251,125 | B1 | 6/2001 | KenKnight et al. |
| 6,312,399 | B1 | 11/2001 | Lurie et al. |
| 6,360,125 | B1 | 3/2002 | Weil et al. |
| 6,539,256 | B1 | 3/2003 | KenKnight et al. |
| 7,074,199 | B2 | 7/2006 | Halperin et al. |
| 7,186,225 | B2 | 3/2007 | Kelly et al. |
| 7,272,441 | B1 | 9/2007 | Chapman et al. |
| 2001/0047140 | A1* | 11/2001 | Freeman ........................ 601/41 |
| 2003/0233129 | A1* | 12/2003 | Matos ................................ 607/5 |
| 2004/0162587 | A1* | 8/2004 | Hampton et al. ................. 607/5 |
| 2004/0230140 | A1 | 11/2004 | Steen |
| 2005/0075531 | A1* | 4/2005 | Loeb et al. ...................... 600/17 |
| 2005/0131465 | A1 | 6/2005 | Freeman et al. |
| 2006/0155222 | A1 | 7/2006 | Sherman et al. |
| 2007/0060785 | A1* | 3/2007 | Freeman et al. ................. 600/16 |

FOREIGN PATENT DOCUMENTS

| WO | WO 02/091905 | 11/2002 |
| WO | WO 2005/021089 | 3/2005 |
| WO | WO 2006/016289 | 2/2006 |
| WO | WO 2007/033050 | 3/2007 |

OTHER PUBLICATIONS

Abella et al., Chest Compression Rates During Cardiopulmonary Resuscitation Are Suboptimal, Circulation, 111:428-434 (2005).
Eftestol et al., "Predicting Outcome of Defibrillation by Spectral Characterization and Nonparametric Classification of Ventricular Fibrillation in Patients With Out-of-Hospital Cardiac Arrest," Circulation, 102:1523-1529 (2000).
Pinsky et al., "Hemodynamic effects of cardiac cycle-specific increases in intrathoracic pressure," J. Appl. Physiol., 60(2):604-612 (1986).
Sato et al., "Adverse effects of interrupting precordial compression during cardiopulmonary resuscitation," Crit Care Med, vol. 25, No. 5, pp. 733-736 (1997).
Yu et al., "Adverse Outcomes of Interrupted Precordial Compression During Automated Defibrillation," Circulation, 106:368-372 (2002).

* cited by examiner

*Primary Examiner* — Nicole F Lavert
(74) *Attorney, Agent, or Firm* — Fish & Richardson P.C.

(57) ABSTRACT

A resuscitation system for use by a rescuer for resuscitating a patient having a ventricular arrhythmia, comprising circuitry and processing configured for detection of chest compression/phase timing information indicative of the start of the decompression phase, circuitry and processing configured for delivery of electromagnetic therapy for the termination of ventricular arrhythmias, wherein the circuitry and processing for the delivery of electromagnetic therapy utilizes the chest compression phase timing information to initiate delivery of the electromagnetic therapy within 300 milliseconds of the start of the decompression phase.

21 Claims, 1 Drawing Sheet

System Block Diagram

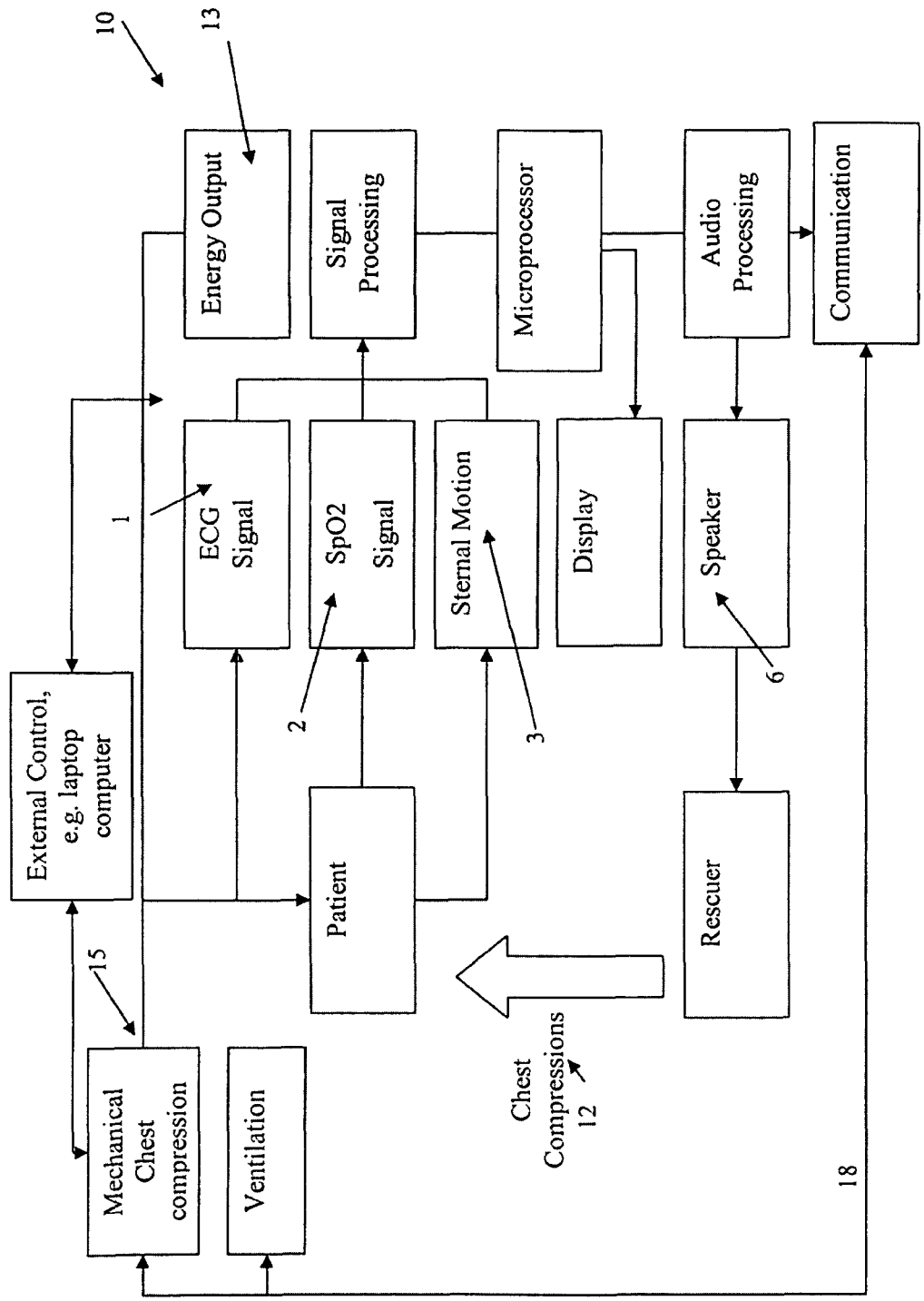

SYNCHRONIZATION OF DEFIBRILLATION AND CHEST COMPRESSIONS

CROSS-REFERENCE TO RELATED APPLICATIONS

This application claims priority to U.S. Application Ser. No. 61/001,347, filed on Nov. 1, 2007.

TECHNICAL FIELD

This invention relates to the field of medical devices for cardiopulmonary resuscitation (CPR) and defibrillation and, more particularly, to synchronization of the defibrillation shock to the chest compression cycle.

BACKGROUND

There are many different kinds of abnormal heart rhythms, some of which can be treated by defibrillation therapy ("shockable rhythms") and some which cannot (non-shockable rhythms"). For example, most ECG rhythms that produce significant cardiac output are considered non-shockable (examples include normal sinus rhythms, certain bradycardias, and sinus tachycardias). There are also several abnormal ECG rhythms that do not result in significant cardiac output but are still considered non-shockable, since defibrillation treatment is usually ineffective under these conditions. Examples of these non-shockable rhythms include asystole, electromechanical disassociation (EMD) and other pulseless electrical activity (PEA). Although a patient cannot remain alive with these non-viable, non-shockable rhythms, applying shocks will not help convert the rhythm. The primary examples of shockable rhythms, for which the caregiver should perform defibrillation, include ventricular fibrillation, ventricular tachycardia, and ventricular flutter.

Resuscitation treatments for patients suffering from cardiac arrest generally include clearing and opening the patient's airway, providing rescue breathing for the patient, and applying chest compressions to provide blood flow to the victim's heart, brain and other vital organs. If the patient has a shockable heart rhythm, resuscitation also may include defibrillation therapy. The term basic life support (BLS) involves all the following elements: initial assessment; airway maintenance; expired air ventilation (rescue breathing); and chest compression. When all three (airway breathing, and circulation, including chest compressions) are combined, the term cardiopulmonary resuscitation (CPR) is used.

After using a defibrillator to apply one or more shocks to a patient who has a shockable ECG rhythm, the patient may nevertheless remain unconscious, in a shockable or non-shockable, perfusing or non-perfusing rhythm. If a non-perfusing rhythm is present, the caregiver may then resort to performing CPR for a period of time in order to provide continuing blood flow and oxygen to the patient's heart, brain and other vital organs. If a shockable rhythm continues to exist or develops during the delivery of CPR, further defibrillation attempts may be undertaken following this period of cardiopulmonary resuscitation. As long as the patient remains unconscious and without effective circulation, the caregiver can alternate between use of the defibrillator (for analyzing the electrical rhythm and possibly applying a shock) and performing cardio-pulmonary resuscitation (CPR). CPR generally involves a repeating pattern of five or fifteen chest compressions followed by a pause during which two rescue breaths are given.

It has recently been recognized that good chest compressions during CPR is essential to saving more victims of cardiac arrest (*Circulation.* 2005:111:428-434). In the cited study, researchers found that in 36.9% of the total number of segments, compression rates were less than 80 compressions per minute (cpm), and 21.7% had rates of less than 70 cpm. The compression rate recommended by the American Heart Association in their guidelines is greater than 100 cpm. In the study, higher chest compression rates were significantly correlated with initial return of spontaneous circulation (mean chest compression rates for initial survivors and non-survivors, 90±17 and 79±18 cpm, respectively; P=0.0033). Further, this study was performed using well-trained rescuers, including nurses and physicians, indicating that the problem of poor compression rates is widespread.

Many studies have reported that the discontinuation of chest compressions, such as is commonly done for ECG analysis, can significantly reduce the recovery rate of spontaneous circulation and 24-hour survival rate. These studies include "Adverse effects of interrupting precordial compression during cardiopulmonary resuscitation" by Sato et al. (Critical Care Medicine, Volume 25(5), May 1997, pp 733-736); "Adverse Outcomes of Interrupted Precordial Compression During Automated Defibrillation" by Yu el al. (Circulation, 2002); and "Predicting Outcome of Defibrillation by Spectral Characterization and Nonparametric Classification of Ventricular Fibrillation in Patients With Out-of-Hospital Cardiac Arrest" by Eftestøl et al. (Circulation, 2002).

Because of safety issues with delivery of a high voltage defibrillation shocks with voltages of 1000-2000 volts, rescuers are taught to cease chest compressions and remove their hands from the victim's chest before initiating the defibrillation shock. U.S. Pat. No. 4,198,963 describes the potential beneficial effect of synchronizing the defibrillation shock with the chest compression cycle of a mechanical chest compressor. The patent specifically teaches that the beneficial effect occurs only when the defibrillation current is applied to the patient's heart only during the systolic portion of the compression cycle of the compressor. U.S. Pat. Nos. 5,626, 618 and 7,186,225 similarly discuss the potential beneficial effects synchronizing the defibrillation shock timing to the systolic portion of the compression cycle postulating that the reduced heart chamber volume during systole improves the current distribution during the shock. However, in spite of the ready availability of defibrillators and mechanical chest compression devices for nearly three decades, the beneficial effect posed by the prior art has remained hypothetical.

In the context of automatic, mechanical compression systems, it has long been recognized that there are beneficial effects of synchronizing cardiac compression and ventilation cycles to the cardiac cycle. M. R. Pinsky, "Hemodynamic effects of cardiac cycle-specific increases in intrathoracic pressure", Journal of Applied Physiology (Volume 60(2), pages 604-612, February 1986).

SUMMARY

It has been discovered by the inventors that delivery of the defibrillation shock during the early portion (approximately the first 300 milliseconds) of the decompression (diastolic) phase of the chest compression cycle will generally improve the likelihood of success of the delivered shock. The decompression phase begins when the rescuer reduces compression force on the chest, allowing the chest to rise, and the heart to expand.

In general the invention features a resuscitation system for use by a rescuer for resuscitating a patient having a ventricular arrhythmia, comprising circuitry and processing configured for detection of chest compression phase and timing information indicative of the start of the decompression phase, circuitry and processing configured for delivery of electromagnetic therapy for the termination of ventricular arrhythmias, wherein the circuitry and processing for the delivery of electromagnetic therapy utilizes the chest compression phase and timing information to initiate delivery of the electromagnetic therapy within 300 milliseconds of the start of the decompression phase.

In preferred implementations one or more of the following are incorporated. Delivery of electromagnetic therapy is initiated within 25-250 milliseconds of the start of the decompression phase. The electromagnetic therapy is electrical defibrillation. The electromagnetic therapy is magnetic defibrillation. Chest compressions are delivered by a mechanical chest compressor. The mechanical chest compression and defibrillator are configured in separate housings. The mechanical chest compression and the defibrillator are integrated into a common housing. Compressions are delivered by manual compressions. Circuitry and processing for the detection of chest compression phase timing information includes a pressure sensor. Circuitry and processing for the detection of chest compression phase timing information includes an accelerometer. Acceleration zero crossing is used for compression phase detection. Feedback is provided for optimization of upstroke velocity. The resuscitation system further comprises an electrically insulating layer that extends over the surface of the patient to allow for delivery of manual compressions during defibrillation. The electrically insulating layer is incorporated into the structure of the defibrillation electrodes. Compressions are synchronized to electrocardiographic activity. The electrocardiographic activity is coarse Ventriculsr LeF. The resuscitation system further comprises spectral analysis of the electrocardiographic activity. The resuscitation system further comprises filtering of the electrocardiographic activity for removal of artifact due to chest compressions. Electromagnetic therapy comprises pacing. Electromagnetic therapy comprises a defibrillation shock and the defibrillation shock is also synchronized to the ventilation cycle. The ventilation expiratory phase is concluded within 2 seconds of delivery of the defibrillation shock.

DESCRIPTION OF DRAWINGS

FIG. 1 is a system block diagram.

DETAILED DESCRIPTION

There are a great many different implementations of the invention possible, too many to possibly describe-herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

This discovery that the defibrillation shock should be synchronized with the early portion of the decompression (diastolic) phase of chest compressions was in part the result of the development by the inventors of a new method for testing of defibrillation thresholds (DFTs). When comparing the efficacy of a therapeutic intervention to an experimental control in the animal model, the DFT is measured for treatment and control separately and then the DFT levels are compared. A so-called DFT50 is the defibrillation energy for a particular treatment at which on average the shock success rate is 50%. To achieve statistical significance, multiple DFTs are performed in sequence with the order of tests between treatment and control randomized. Unfortunately, the process of induction of ventricular fibrillation in the experimental animal is physiologically deleterious due to the extended periods of anoxia. As a result, the underlying state of the animal and the associated statistics is non-stationary and differences in treatment effect are often obfuscated by unavoidable drift in the DFTs as the animal's physiological state degrades over time.

The inventors have developed a method whereby the treatments that are desired to be compared are grouped together with a small number (on the order of 1-5) of repeated measures in random sequence with all defibrillation levels for the treatments in the group set to the same level and a block size small enough so that the statistics of the animal's state can be considered stationary. Then a standard DFT50 test would be performed on the block of treatments. So, as an example, if there are four different synchronization phases that are to be compared, each block would have 3 measures for each of the different phases, for a total of 12 shocks, with each of the shocks set to the same energy level. If it is found that the shock success rate for the group of 12 is above 50% then the energy level is dropped for the next block of 12; if the shock success rate is below 50%, then the energy level of the next block will be increased. In this manner, the aggregate shock success rate is maintained at 50% over time. If there is a therapeutic difference between the various treatments, it can be detected using standard tests on proportions such as the Chi-square test with a greater degree of sensitivity and repeatability.

In a study of 15 swine, defibrillation was synchronized to various points in the chest compression cycle. The study was carried out in a 25 Kg porcine AC-induced VF model. For each porcine model, the following four different coupling phases were tested: CPa: 20 ms before the onset of compression; CPb: 130 ms after the onset of compression; CPc: 20 ms before the onset of decompression; CPd: 130 ms after the onset of decompression.

Each animal was preanesthetized with an IM mixture of Telazol (4.4 mg/Kg), Ketamine (2.2 mg/Kg), and xylazine (2.2 mg/Kg) or the combination of Ketamine (20 mg/Kg) and xylazine (2 mg/Kg). Atropine (0.05 mg/Kg) given IM was used to dry oral-tracheal secretion and prevent bradycardia during intubation or cut-down surgery. Following the placement of a venous line in the ear (lateral or medial auricular vein), isoflurane anesthesia (0.8-3.2%) was administered. The animal was then be intubated using VYGON CFV endotracheal tube model and be supplied with constant O2 flow of 5 L/min using the constant pressure technique. A HP Doppler transesophageal transducer was also placed into its esophagus and was connected to a HP echocardiographic system to record and characterize bemodynamic and dynamic changes in heart anatomy during AutoPulse (mechanical chest compressor) CPR. Animals were monitored by heart rate, corneal reflexes, and by arterial pressures throughout the experiment.

Femoral or jugular arterial and venous access sheaths was placed, using a cut-down or percutaneous access approach. The arterial sheath was used to continuously monitor systemic blood pressure during the procedure. The peripheral venous sheath was used to administer intravenous fluids throughout the procedure. A 4 French pigtail catheter was advanced through the femoral arterial sheath. The LV pressure was measured using the pigtail catheter (Bard, Murray Hill, N.J.) positioned apically in the left ventricle through the femoral artery. The catheter was connected to a pressure transducer (Schneider Namic, Glens Falls, N.Y.) and pressure recordings were acquired and digitized using the MP100 Data Acquisition System.

Following preparation, the animal was put on the mechanical chest compressor (AutoPulse, ZOLL Medical MA). The device delivers a compression via a spindle take-up system of a load-distributing band that is wrapped around the subject's thorax. A force transducer that is integral to the AutoPulse measures the downward forces produced by the compression cycles delivered by the AutoPulse. A continuous analog signal proportional to force measured by the force transducer is output via a connector on the AutoPulse.

Referring to FIG. 1, in the preferred embodiment, synchronization between the chest compression 12 and defibrillation is accomplished by a communications connection 18, via either a hardwire or wireless connection, between a separate defibrillator 10 and a mechanical chest compression device 15. In some implementations, these devices are the E-Series defibrillator (ZOLL Medical, Chelmsford Mass.) and the AutoPulse mechanical chest compressor (ZOLL Circulation, Sunnyvale Calif.). There are two connectors on the AutoPulse: 1) the force transducer output (FTO) connector; and 2) the high voltage (HV) connector. Communication 18 is achieved via a hardwired connection of the defibrillator high voltage (DHV) cable into the FrO connector. Self adhesive defibrillation pads are attached to the patient for delivery of therapeutic defibrillation current, and are connected to the HV connector. Inside the AutoPulse, the high voltage wires of the DHV cable are interconnected with the HV connector output to the defibrillation pads. The transducer output from the AutoPulse are connected to analog input lines on the DHV cable via the FTO connector.

In the experimental protocol to test efficacy of synchronization of defibrillation and compression, ventricular fibrillation (VF) was induced using direct current supplied by a 9 V battery and applied to the right ventricle, and was permitted to persist for 30 seconds prior to an AutoPulse CPR. Following the 30 second period of AutoPulse CPR, a predetermined shock energy was delivered to attempt to defibrillate the VF in a predetermined coupling phase. If the shock fails to defibrillate, then a rescue shock was delivered using the same defibrillation device used to deliver the failed defibrillation shock. The outcome of the shock was recorded, the animal was permitted to stabilize hemodynamically for four minutes, and then the sequence (fibrillate, AutoPulse CPR, defibrillate, rescue) was performed using the next predetermined defibrillation shock in a predetermined coupling phase. The detailed protocol follows:

For each pig:
1. Record 5 seconds of AutoPulse load cell signal (without defib shocks), play it back and check if shocking phases (77 ms, 365 ms, 526 ms, 564 ms, 688 ms) need to be adjusted;
2. Select first test energy=1.7*weight (kg), rounding off to 5;
3. Place a pair of Stat.padz, adult Defib pads in lateral-to-lateral configuration.
4. Randomize shocking sequences (77 ms, 365 ms, 526 ms, 564 ms, 688 ms) to select a testing phase; induce VF;
6. Wait for 5 seconds, if VF is sustained, turn on AutoPulse;
7. At 5 seconds after AutoPulse is turned on, charge defibrillator, also give 2 manual ventilations;
8. At 10 seconds after defibrillator is charged, deliver the test energy in the testing phase;
9. If VF is converted, stop AutoPulse and record delivered Joule, impedance and current in data spreadsheet; if defibrillation fails, continue AutoPulse, deliver a double energy for rescue shock; if defibrillation fails again, deliver 200 J for rescue shock. After 5 rescue shocks fail, perform 1 minute AutoPulse CPR before delivering another round of rescue shocks up to 5 times;
10. Repeat step 4 and step 9 until all the 5 testing phases are done;
11. Repeat steps 4 to 10 one more time;
12. Calculate success probability on the aggregated testing results of the above 2 shocking sequences;
13. If the probability<50%, the next test energy was increased by 10 J; otherwise, decreased by 10 J;
14. Change defib pads;
15. Repeat steps 4 to 12;
16. If the probability<50%, the next test energy was increased by 5 J; otherwise, decreased by 5 J;
17. Repeat steps 4 to 11;
18. Select one from the above 3 used test energies which resulted in a success probability closest to 50% as the next test energy;
19. Repeat steps 4 to 10 for 6 times or until the animal is exhausted;

Randomization for each block was as follows: for each porcine model, the order of four predetermined coupling phases was randomized using a randomization schedule based on a predetermined random permutation of 4. A chi square test is then performed on all blocks having an aggregate shock success rate between 40 and 60 percent.

It was found that the early decompression phase yielded the best shock success rates, while the early compression phase yielded the least effective shock success rates. It was found that early decompression phase had nearly double the shock success rate of early compression (70.3% vs. 36.4%, p=0.0003, odds ratio (OR)=4.266, OR confidence interval=[1.916-9.496]).

In some implementations, the defibrillator electronics 10 is incorporated directly into the mechanical chest compression device 15. That configuration has the benefit of reducing the amount of equipment that the rescuer needs to carry to the scene of a cardiac arrest. The battery power supply for the chest compression device then is used for both compressions as well as defibrillation and other physiological monitoring such as pulse oximetry 2, electrocardiograms 1, and capnography, which are commonly found in defibrillators.

In other implementations, chest compressions 12 may be accomplished by manual compressions. In these implantations, there is no need for a mechanical chest compressor 15. Detection of the exact phase of the compression cycle can be accomplished by a sensor capable of detection of chest compressions 3. One embodiment is a pressure sensor placed under the patient or under the rescuer's hands during manual compressions. Compression phase detection may also be accomplished by the use of an accelerometer placed beneath the rescuer's hands during chest compressions as described in U.S. Pat. No. 7,074,199. Edge detection schemes such as bandpass filtering followed by rectification and dynamic thresholding, known to those skilled in the art, can then be performed on the compression signal to determine the start of the decompression phase and then delaying from that point to the optimal timing for initiating delivery of the defibrillation shock. Delay from detection of the start of the decompression phase (diastole) to initiation of delivery of the defibrillation shock can be as brief as 1-2 milliseconds up to only approximately 300 milliseconds (preferably 125 milliseconds). To minimize the latency of the phase detection algorithm, zero crossing detection of the raw accelerometer signal is preferably used for compression phase detection.

Achieving maximal beneficial effect with manual compressions will likely require as short a time as possible for the upstroke phase. Duration of the upstroke phase can be minimized by increasing the upstroke velocity of decompressions in the manual compression cycle. To accomplish this both visual and/or verbal prompting is incorporated into the defibrillator to achieve, on a real-time basis, improvement in the upstroke velocity of the rescuer's compressions.

One prohibitive factor with the synchronization of defibrillation to manual compressions is that the defibrillation shock generates approximately 2000 volts. Touching the patient directly during a defibrillation shock will not harm the rescuer, but it can generate a significant amount of discomfort. It is thus desirable to incorporate an electrically insulating protection layer that extends over the surface of the patient so that manual compressions may continue safely and unabated during the defibrillation shock, as is described in U.S. Pat. No. 6,360,125.

It is also desirable to synchronize compressions with the electrocardiographic (ECG) activity 1 of particularly coarse ventricular fibrillation (VF) and to synchronize the defibrillation shock 13 and decompression phase to the maximum positive dV/dt (informally "upstroke") of the ECG 1 for coarse VF. Synchronization of shocks with ECG activity 1 is well know to those skilled in the art, and in particular synchronization to ECG activity 1 of VF has been described in U.S. Pat. Nos. 6,539,256, 6,251,125 and 6,112,117, but none describes the beneficial effect of synchronizing all three elements. Coarse VF may be defined simply as VF whose absolute amplitude exceeds some threshold such as 0.75 millivolts RMS. Preferably, however, determination of coarseness may also incorporate such shock prediction measures such as that disclosed in U.S. Pat. No. 5,957,856 to determine whether or not the ECG 1 rhythm and underlying physiological state of the patient is viable enough for delivery of a shock.

Synchronization of the compression phase with the ECG 1 requires the ability to sufficiently filter out the ECG artifact that results from chest compressions. A preferred implementation of this is described in U.S. Pat. No. 7,074,199. The mechanical chest compressor can easily synchronize to the ECG activity with such filtering means. Delivery of compressions synchronized to ECG activity with manual compressions is not accomplished as easily, but methods exist for providing the appropriate feedback to achieve synchronization of manual compression phase to the ECG activity as described in U.S. Pat. No. 7,650,181.

Referring to FIG. 1, one or more sensors or instruments 1, 2, 3 are used to acquire physiological signals from the patient. Pre-processing of certain signals may be required to derive relevant measurements or remove artifacts. For example, CPR artifact may be removed from the ECG signal using known techniques. The time of onset (start) of a chest compression can be determined in other ways, including from transthoracic impedance, which is typically measured by AEDs, or from the artifact generated in the ECG by the chest compression. A speaker 6 generates a feedback tone (one possible type of feedback cue), which we also refer to as the compression rate tone (CRT), at the desired rate and timing with regard to the cardiac cycle.

Synchronization may be achieved either through direct communication between devices such as an analog signal or a serial Universal Serial Bus (USB) interface or synchronization can be achieved wirelessly using a low-latency wireless protocol such as the so-called ZIGBEE, IEEE 802.15.4 protocol standard.

Pacing may also be combined, in some implementations, with manual compressions as a means of augmenting the rescuer's mechanical compressions with the electrically-induced contractions of the myocardium. During a resuscitation, the heart is in a state of profound ischemia resulting in a flacidity and loss of tone as lactate builds up in the myocardium and the tissue pH drops. As a result of the loss of tone, the heart becomes a less-effective pump structure for generating blood flow during manual chest compressions. Drugs such as epinephrine act to improve tone, but because they are delivered venously, their action may take 2-3 minutes during cardiac arrest, when the only blood flow is that induced by the chest compressions. Pacing that may or may not be sufficient to actually cause a satisfactory hemodynamic response as a result of the metabolically compromised state of the myocardium can sufficiently improve the tone of the myocardium immediately prior to, and synchronized with, the mechanical compression without the therapeutic delay experienced with drugs such as epinephrine. This instantaneous improvement in myocardial tone can substantially improve the hemodynamic effectiveness of the mechanical compression.

In another embodiment, compressions and shock are additionally synchronized and properly phased to the ventilatory cycle. At the time of shock, it is desirable that there not be a ventilation in progress. Preferable sequencing is for ventilation expiratory cycle to complete in the decompression phase of the compression cycle immediately proceeding the compression cycle during which the synchronized shock takes place. The ventilator will preferably receive a synchronization signal from defibrillator 10.

Many other implementations of the invention other than those described above are within the invention, which is defined by the following claims.

What is claimed is:

1. A resuscitation system for use by a rescuer for resuscitating a patient having a ventricular arrhythmia, comprising:
   circuitry and processing configured for detection of chest compression/phase timing information indicative of the start of a decompression phase;
   circuitry and processing configured for delivery of electromagnetic therapy for the termination of ventricular arrhythmias;
   wherein the circuitry and processing for the delivery of electromagnetic therapy utilizes the chest compression phase timing information to initiate delivery of the electromagnetic therapy within 300 milliseconds of the start of the decompression phase.

2. The system of claim 1 wherein the delivery of electromagnetic therapy is initiated within 25-250 milliseconds of the start of the decompression phase.

3. The system of claim 1 wherein the electromagnetic therapy is electrical defibrillation.

4. The system of claim 1 wherein the electromagnetic therapy is magnetic defibrillation.

5. The system of claim 1 wherein the chest compressions are delivered by a mechanical chest compressor.

6. The system of claim 5 wherein the mechanical chest compression and defibrillator are configured in separate housings.

7. The system of claim 5 wherein the mechanical chest compression and the defibrillator are integrated into a common housing.

8. The system of claim 1 wherein the compressions are delivered by manual compressions.

9. The system of claim 8 wherein the circuitry and processing for the detection of chest compression phase timing information further comprises a pressure sensor.

10. The system of claim 8 wherein the circuitry and processing for the detection of chest compression phase timing information further comprises an accelerometer.

11. The system of claim 10 wherein acceleration zero crossing is used for compression phase detection.

12. The system of claim 8 wherein feedback is provided for optimization of upstroke velocity.

13. The system of claim 1 further comprising an electrically insulating layer that is adapted to extend over a surface of the patient to allow for delivery of manual compressions during defibrillation.

14. The system of claim 13 wherein the electrically insulating layer is incorporated into the structure of defibrillation electrodes.

15. The system of claim 1 wherein compressions are synchronized to electrocardiographic activity.

16. The system of claim 15 wherein the electrocardiographic activity is coarse VF.

17. The system of claim 15 further comprising spectral analysis of the electrocardiographic activity.

18. The system of claim 15 further comprising filtering of the electrocardiographic activity for removal of artifact due to chest compressions.

19. The system of claim 1 wherein the electromagnetic therapy comprises pacing.

20. The system of claim 1 wherein the electromagnetic therapy comprises a defibrillation shock and the defibrillation shock is also synchronized to a ventilation cycle.

21. The system of claim 20 wherein the ventilation expiratory phase is concluded within 2 seconds of delivery of the defibrillation shock.

* * * * *

UNITED STATES PATENT AND TRADEMARK OFFICE
CERTIFICATE OF CORRECTION

PATENT NO. : 8,478,401 B2
APPLICATION NO. : 12/263813
DATED : July 2, 2013
INVENTOR(S) : Freeman Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 858 days.

Signed and Sealed this
Twenty-seventh Day of January, 2015

Michelle K. Lee
*Deputy Director of the United States Patent and Trademark Office*